United States Patent [19]

Vaguine

[11] 4,397,313

[45] Aug. 9, 1983

[54] MULTIPLE MICROWAVE APPLICATOR SYSTEM AND METHOD FOR MICROWAVE HYPERTHERMIA TREATMENT

[75] Inventor: Victor A. Vaguine, Dallas, Tex.

[73] Assignee: Clini-Therm Corporation, Dallas, Tex.

[21] Appl. No.: 289,126

[22] Filed: Aug. 3, 1981

[51] Int. Cl.³ ............................................. A61N 5/02
[52] U.S. Cl. .................................. 128/399; 128/401; 128/783; 128/804
[58] Field of Search ............ 128/399, 400, 401, 419N, 128/422, 736, 783, 804; 219/10.55 A, 10.55 F, 10.55 M, 10.55 R; 343/757, 758, 759, 760, 761, 762

[56] References Cited

U.S. PATENT DOCUMENTS 4,197,860 4/1980 Sterzer ................................. 128/804
4,316,474 2/1982 Spethmann .................... 219/10.55 F

*Primary Examiner*—Richard J. Apley
*Assistant Examiner*—George Yanulis
*Attorney, Agent, or Firm*—Richards, Harris & Medlock

[57] ABSTRACT

Multiple microwave applicators are configured to optimize the treatment in a hyperthermia system. Individual applicators are positioned for incrementally varying the treatment field size by the addition or subtraction of individual applicators. A fan beam geometric configuration may be utilized with individual applicators for producing a concave electric field for focusing the electromagnetic energy at a particular region of the body. The microwave applicator system may be positioned either in direct or indirect contact with a treatment area by positioning individual applicators to conform to the contours of the surface treatment area. The applicators may be combined to provide a continuing electromagnetic field pattern.

23 Claims, 8 Drawing Figures

MULTIPLE MICROWAVE APPLICATOR SYSTEM AND METHOD FOR MICROWAVE HYPERTHERMIA TREATMENT

TECHNICAL FIELD

This invention relates to microwave waveguide applicators for use in a hyperthermia treatment system, and more particularly to a plurality of waveguide microwave applicators aligned for shaping the electromagnetic field in a treatment area and for allowing the system to be operated in the direct contact modality.

BACKGROUND ART

Hyperthermia is the heating of living tissue for therapeutic purposes. Hyperthermia has been used as a method of treating cancer by means of raising the temperature of a tumor locally, or a region of the body in which the tumor is located, or of the whole body. It has long been known that high heat can trigger the natural regression and/or remission of tumors. Because of its effect on cancer cells, hyperthermia may be used as an independent therapy or in conjunction with other cancer therapies, such as radiation, surgery, chemotherapy, and immunotherapy to enhance the effectiveness of these therapeutic modalities. Current hyperthermia techniques used in cancer therapy include regional perfusion with heated fluids, microwave heating, fluid immersion, low frequency (RF) current fields, and ultrasound.

Three of the most common types of currently used hyperthermia techniques involve radio frequency, microwaves and ultrasound. Radio frequency and microwave equipment may be used for local, regional and whole body heating. Ultrasound can also be used for local and regional heating.

Microwave hyperthermia systems have been developed utilizing direct contact microwave waveguide applicators. The depth of penetration of the microwave energy is frequency-dependent, and the penetration is also a function of tissue composition and anatomical structure. The design of the microwave waveguide applicator radiating antenna influences the thermal distribution. In addition, sharp changes in patient contour within the heated area, as in the head and neck region, will have an influence on the thermal distribution.

Multiple microwave applicator systems for hyperthermia application have been previously developed. One such multiple applicator system is a combination of twelve applicators installed inside of three adjacent stacked rings with four applicators in each ring. Since each applicator is powered from an independent power generator, the system operates in the incoherent mode for its operating frequency of 433 MHz. As a result, the overall heating pattern produced by the multiple applicators is a combination of the individual heating patterns produced by each separate applicator. Such an array of multiple microwave applicators has a fixed geometry with no direct contact possible between the patient and the open end of the applicators. Further, the electromagnetic radiation surrounds the area of the patient's body to be treated, heating all healthy tissue within the field of radiation as well as the tumor. This prior art hyperthermia treatment system is capable of operating only in the incoherent mode at single frequency, and it is capable of use only for regional hyperthermia treatment.

In another existing multiple microwave applicator system for hyperthermia treatment, at least eight applicators are provided in an annular phase array system powered from the same generator for operation only in the coherent mode. In the operation of this system, the heating pattern from the annular array of applicators is a result of the super-position of electromagnetic waves from all eight applicators in the system. The electromagnetic field configuration is a convergent cylindrical wave with the electric field within the applicator parallel to the applicator system axis the body of the patient placed within the annular array of applicators. However, the electric field outside the boundary of the applicator is not parallel and will enter and exit the surface of the body at an angle. This can produce overheating in area where the electric field breaks the boundary of the surface of the patient's body. The system is designed for operation with a frequency range of approximately 40 to 100 MHz. As in the other multiple applicator system, the geometry of the applicators in this system is fixed and direct contact modality is possible between the open end of the applicator and the patient only through a thick water pad. The electromagnet energy delivered to the site of the tumor in the body results in heating (radiation) of all the tissues, healthy cells and abnormal or malignant cells, within the 360° annular energy field pattern, unnecessarily heating a considerable amount of healthy tissue. The annular phase array system is limited in that it is not capable of being operated in the incoherent modality and is capable for use only in regional hyperthermia treatment.

A need has thus arisen for a multiple microwave applicator system for hyperthermia treatment with a flexible geometry for altering the field pattern for enhancing the shape of the field and the heating pattern for the treatment area. A need has also arisen for a multiple microwave applicator system to be operated in direct contact modality with the open end of the applicators contacting the patient or contacting the cooling belt surrounding the patient treatment area. A need has also arisen for contouring the applicators and electromagnetic field to the body treatment area for improving the focusing of the heating pattern and reducing radiation leakage. A multiple microwave applicator system operated in the direct contact modality reduces the unnecessary heating of healthy tissue in non-direct modality. A need has also arisen for a multiple applicator system for use in a hyperthermia treatment system capable of being operated in either the coherent or incoherent mode. A need has further arisen for a multiple applicator system for use in hyperthemia treatment that generates an electric field substantially parallel to the contour of the patient body section treated and one that is capable for use in local and regional hyperthermia treatments.

SUMMARY OF INVENTION

The apparatus and the method of the present invention is an improvement over the above-described prior art apparatus and method of hyperthermia treatment. In the present invention, a plurality of waveguide applicators are aligned and configured to shape the electromagnetic field pattern and resultant heat treatment pattern. Rectangular waveguides are illustrated and described in the preferred embodiment, but cylindrical or elliptical waveguides could also be used. Each applicator operates at the fundamental mode, and a continuous electromagnetic field pattern is produced for the combination of multiple applicators, neglecting the thickness of the metal walls separating individual applicators. The flexible geometry provided by the array of multiple microwave applicators allows the system to be operated in the direct contact mode, or if desired in the non-contact mode. The direct contact mode is advantageous for optimizing individual treatment results, but system efficiency in terms of patient through-put may require operation in the non-contact mode. In operation of rectangular applicators in the $TE_{01}$ mode the multiple applicator system has its magnetic field parallel to the system axis, unlike the prior art systems. This system reduces the overheating where the electric field crosses the boundary between air and the contour of the patient body section. The multiple applicators may also be arranged in a "fan beam" geometric configuration to produce a convergent electromagnetic wave. The convergent fan beam geometry enables the direct contact applicators to be conformed to the various contours of the human body subject to treatment, and it enables the electromagnetic energy to be focused on the tumor while minimizing the region of healthy cells exposed to the elevated temperatures.

The multiple applicator system of the present invention may also be operated in either coherent or incoherent modes of operation. In the case of the incoherent mode of operation, the overall heating pattern is a sum of the individual heating patterns produced by each of the applicators. The incoherent operation in the multiple applicator system of the present invention can be implemented in one of several ways, including independent power sources for each applicator, using phase shifters to randomly shift the phase applied to each applicator in respect to a reference applicator, and use of a coaxial switch to distribute power sequentially from one applicator to another.

In the case of incoherent mode of operation, microwave power is distributed among applicators in any predetermined way in order to optimize treatment and distribution of power is controlled by computer control system during treatment.

The multiple applicator system of the present invention may be utilized in a coherent operation by using a single microwave generator power source. The output from the microwave generator may be divided equally among the applicators by a power divider, and variable phase shifters may adjust each of the applicators with respect to the reference applicator in order to achieve an optimum overall heating pattern for the system.

BRIEF DESCRIPTION OF DRAWINGS

For a more complete understanding of the present invention and the advantages and features thereof, reference is now made to the accompanying Detailed Description taken in conjunction with the following figures in which.

DETAILED DESCRIPTION

Figure 1:
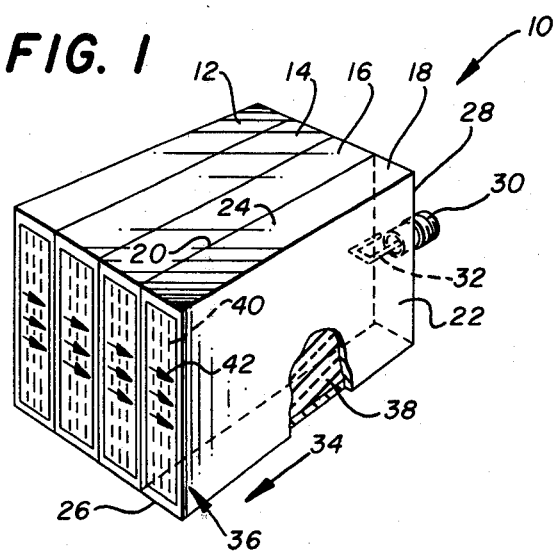
FIG. 1 is a perspective view of one type multiple applicator unit of the present invention assembled from four waveguide applicators.

FIG. 1 illustrates a multiple microwave applicator unit of the present invention, generally identified by the reference numeral 10. Four individual rectangular waveguide applicators 12, 14, 16 and 18 are combined to form the multiple applicator unit 10 of the present invention. Each of the individual rectangular applicators 12–18 typically operates in the $TE_{01}$ mode, although the applicators could be operated in higher order transverse electric modes. The $TE_{01}$ is a fundamental mode used in rectangular waveguides and provides for low frequencies of operation. The waveguide cannot transmit below the cutoff frequency, and the cutoff frequency for this mode is the lowest possible frequency of operation for this particular applicator. The TE mode represents the Transverse Electric mode, wherein the Electric field is transverse to the direction of propagation.

The waveguide applicator 18 is illustrated in phantom view to further explain the operation of the multiple waveguide applicator unit 10. The waveguide applicators 12, 14 and 16 are identical to applicator 18 and the description of waveguide 18 also describes these applicators. Two elongated metal side walls 20 and 22 are joined to upper and lower walls 24 and 26 to form a rectangular waveguide with two side walls 20 and 22 extending longer than the side walls 24 and 26. A closed end 28 of the waveguide applicator 18 is connected to a microwave power source through a microwave coupler 30. A metal loop 32 is connected to the coupler 30 and is positioned at the closed end 28. The metal loop 32 provides magnetic coupling, wherein the metal loop 32 is always located in the maximum magnetic field region at the closed end 28 of the waveguide 18 for the $TE_{01}$ mode of operation independent of the frequency. The electromagnetic wave is propagated in the direction indicated by the arrow 34 from the closed wall 28 to the open end 36 of the applicator 18. The interior of the waveguide 18 may be filled with a low loss dielectric material 38 to reduce the requisite size of the applicator 18. Of course, the waveguides 12–18 can be operated in accordance with the present invention without a low loss dielectric material in the cavities. A suitable dielectric material has been utilized in one embodiment of the invention with a dielectric constant of thirty.

The electromagnetic wave propagated in the direction 34 in the applicator 18 is illustrated at the open end 36 as a magnetic wave 40 parallel to the axis of the applicator 18, and an electric field 42 normal to the axis of the applicator 18. If the thickness of the metal side walls 20 and 22 separating the individual applicators 12–18 is ignored, a continuous electromagnetic field pattern is produced over the entire multiple applicator unit 10. Thus, the combination of the individual applicators 12-18 in a configuration shown in FIG. 1 is equivalent to one large waveguide applicator, for coherent operation where the power is distributed equally and there is no difference in phases among individual applicators. In such an arrangement, the treatment field size can be changed incrementally by adding or subtracting individual applicators from the multiple applicator unit 10.

Figure 2:
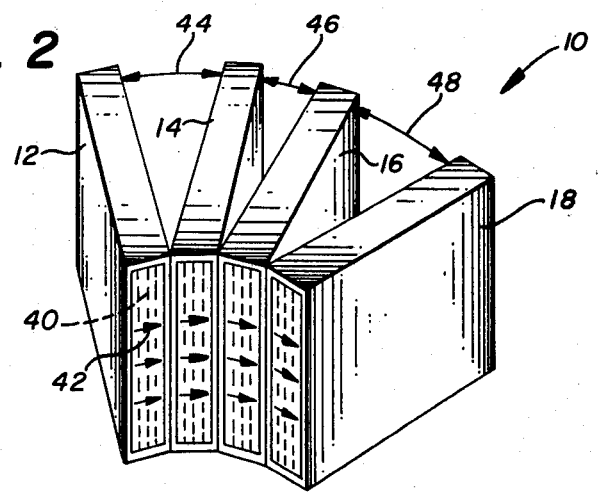
FIG. 2 is a perspective view of a fan beam configured multiple applicator unit of the present invention.

FIG. 2 illustrates the multiple microwave applicator unit 10 of the present invention with individual applicators 12-18 now arranged in a convergent fan beam geometry. The angles of separation 44, 46 and 48 between the applicators 12-14, 14-16 and 16-18 are typically unequal. The individual applicators 12-18 may be arranged into the desired geometry with any suitable mounting means, e.g., a metal plate (not illustrated) with an open slot and adjustable set screws for adjusting and fixing the applicators 12-18 in the desired fan beam geometry.

The normal tendency for an electromagnetic wave is to begin diverging at the boundary of the open ends 36 of each of the applicators 12-18. The ability to arrange the individual applicators of a multiple applicator unit 10 into fan beam geometry configuration illustrated in FIG. 2 enables one to reduce divergency of electromagnetic wave and to focus energy. The angle between the applicators 12-18 can be changed to create different configurations for focusing the energy.

Figure 3:
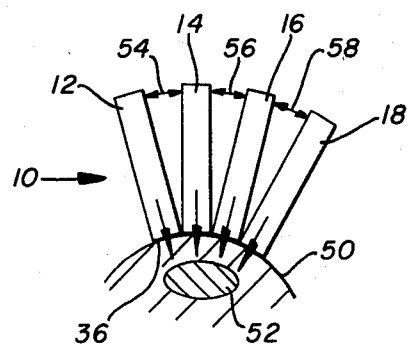
FIG. 3 is a schematic view of an equal angled fan beam configured multiple applicator unit of the present invention for use in a local hyperthermia treatment.

FIG. 3 illustrates a section of human tissue 50 which is the site of a tumor 52 to be subjected to a local hyperthermia treatment. The individual applicators 12-18 of unit 10 have been arranged into a fan beam convergent geometry, wherein the angles between the applicators 54, 56 and 58 are equal. The applicators 12-18 may be mounted on any suitable support for maintaining the applicators in the desired geometric figuration. The opened ends 36 of the applicators 12-18 are brought in direct contact with the treatment area of human tissue 50 to provide the advantages of a direct contact modality, including reduced radiation leakage. Of course, contact via water or fluid filled elastic belts (pads) is also possible.

Figure 4:
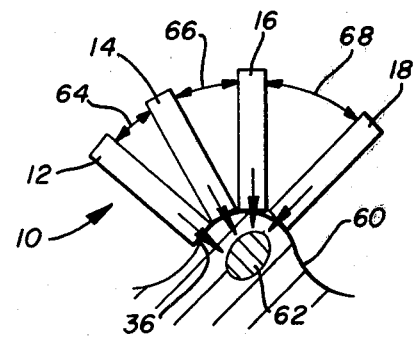
FIG. 4 is a schematic view of an irregular angled fan beam configured multiple applicator of the present invention to conform to the contour of the treatment area of the patient's body for use in a local hyperthermia treatment.

FIG. 4 illustrates a multiple applicator unit 10 of the present invention in direct contact with a treatment area of human tissue 60 which is the site of a tumor 62 for a local hyperthermia treatment. The individual applicators 12-18 forming the multiple applicator unit 10 may be arranged to provide substantially direct contact between the open ends 36 of the individual applicators 12-18 and the contour of the surface area of human tissue 60. The irregular angles 64, 66 and 68 between the individual applicators 12-14, 14-16 and 16-18 enable the applicators to be placed in direct contact with the treatment area, as well as to cause the electromagnetic radiation to be focused at the desired area of treatment within the body. Individual applicators 12-18 may be fixed in the fan beam geometric configuration illustrated by any suitable support mechanism.

Figure 5:
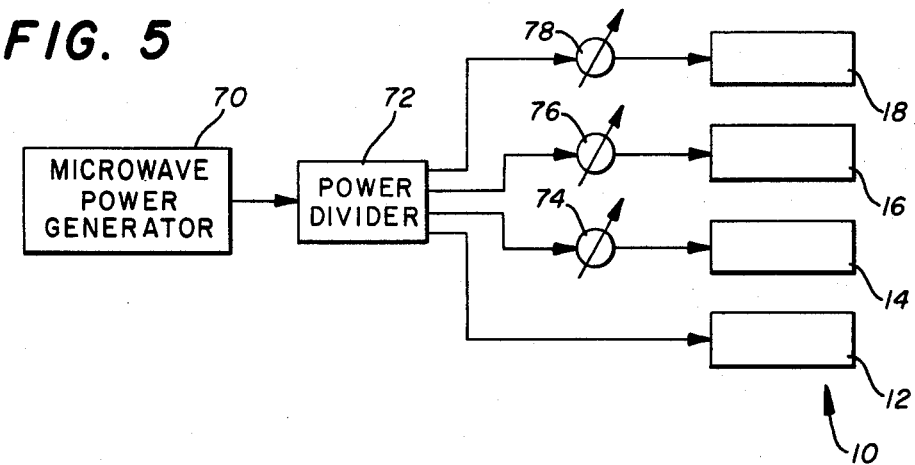
FIG. 5 is a block diagram of a multiple applicator unit of the present invention configured for coherent or incoherent mode of operation.

A hyperthermia treatment system may be operated in either the coherent or incoherent mode by utilizing a multiple applicator unit 10 of the present invention. FIG. 5 illustrates a hyperthermia system operating in the coherent mode. A microwave power generator 70 has its power output equally divided by a power divider 72 to the individual waveguide applicators 12-18 of the multiple applicator unit 10. One of the microwave applicators must be designated as the reference applicator for phase adjusting the other signals in relation to the microwave signal applied to the reference applicator. In FIG. 5, applicator 12 is that reference applicator, and phase shifters 74, 76 and 78 adjust the phase relationship of the microwave signal from the power divider 72 to the other applicator 14, 16 and 18. The variable phase shifters 74, 76 and 78 may be adjusted in respect to the reference phase of the applicator 12 to achieve an optimum heating pattern. The hyperthermia treatment system illustrated in FIG. 5 may also be operated in incoherent modality by randomly and rapidly phase modulating the microwave power utilizing the phase shifters 74, 76 and 78 during a hyperthermia treatment.

Figure 6:
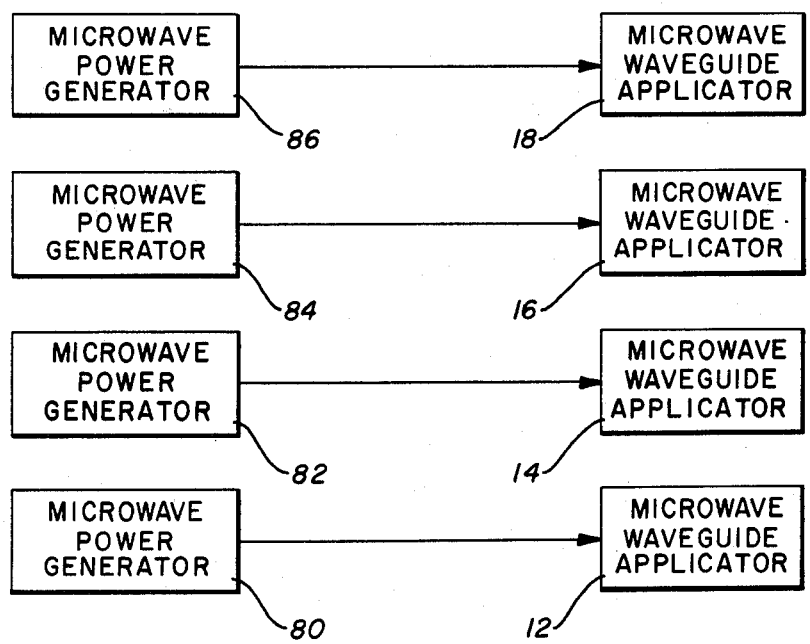
FIG. 6 is a block diagram view of a multiple applicator unit of the present invention configured for incoherent operation.
Figure 7:
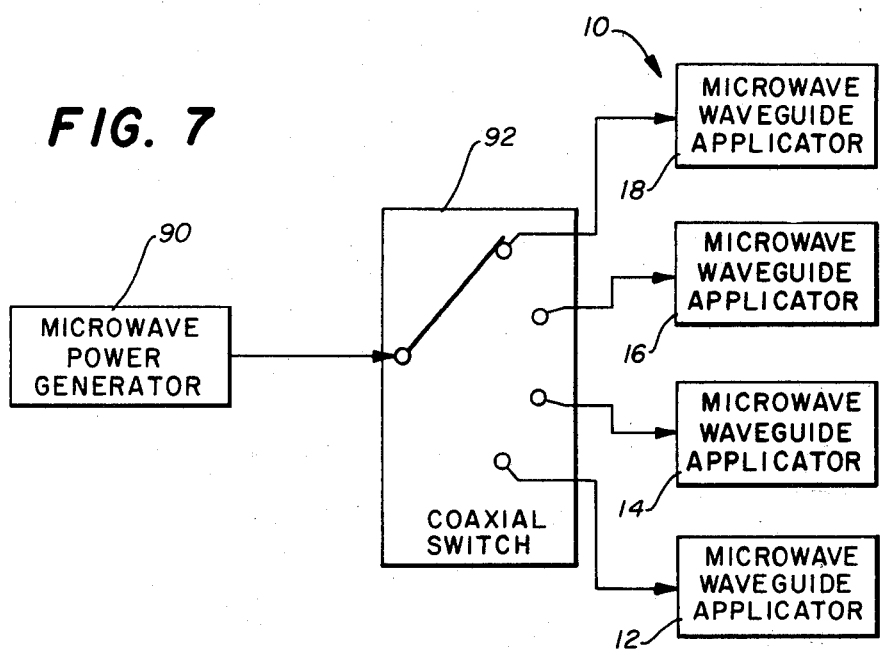
FIG. 7 is a block diagram view of a multiple applicator unit of the present invention configured for incoherent operation with a coaxial switching device and a single power source.

FIGS. 6 and 7 illustrate a hyperthermia treatment system for operation in the incoherent mode. In the incoherent mode of operation, the heating pattern for the multiple applicator 10 is the sum of the individual heating patterns produced by each applicator. In FIG. 6, individual microwave power generators 80, 82 and 84 supply microwave power to the waveguide applicators 12, 14, 16 and 18. FIG. 7 illustrates another embodiment of a hyperthermia treatment system utilizing the multiple applicator unit 10 of the present invention in the incoherent mode of operation. A microwave power generator 90 is connected by a coaxial switching device 92 sequentially to each of the microwave waveguide applicators 12-18.

Figure 8:
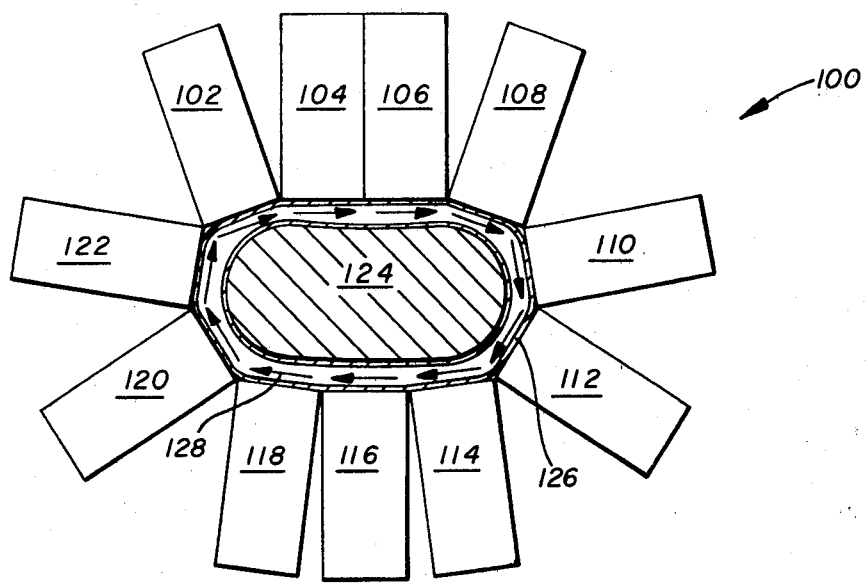
FIG. 8 is a cross-sectional view of a region of a patient's body treated with an array of multiple applicators surrounding the body.

FIG. 8 illustrates a multiple applicator unit 100 of the present invention for use in a regional hyperthermia treatment system. Individual rectangular waveguide applicators 102-122 are positioned to completely surround a region of the patient's body 124 for treatment. An elastic water filled cooling belt 126 surrounds the patient's body region 124 and provides cooling to reduce the temperature of healthy surface tissue. The applicators 102-122 may be positioned around a body treatment area without the cooling belt 126, either in direct or indirect contact modality. The electric field of the applicators 102-122 is indicated by the arrows 128, and the field is substantially parallel to the contour of the treated region of the patient's body 124. The multiple applicator unit 100 for regional hyperthermia treatment is an extension of the multiple applicator unit 10 for local hyperthermia treatment in which the applicators have been added to the unit to surround the treatment site. The multiple applicator unit 100 has its electric field substantially parallel to the contour of the patient's body region 124 and reduces overheating from an electric field crossing the boundary of the patient's surface area.

In the case of the incoherent mode of operation, power input to each of the applicators of the multiple applicator device 10 can be controlled independently or by computer control system with an electronic digital signal processor. The incoherent mode of operation can produce a heating pattern by combining the individual heating patterns produced by each individual applicator. Therefore, in the case of incoherent modality the hyperthermia system can produce an optimized heating pattern by independently controlling the power level to each of the individual applicators of the multiple applicator device 10. Where the focusing of the electromagnetic energy is desired, the coherent mode of operation offers some advantages over the incoherent mode of operation.

In the case of FIG. 7 microwave power is distributed among individual applicators by changing the time relationship between the various applicators. The hyperthermia system of the present invention has its magnetic field parallel to the axis of the patient, and the electric field is orthogonal to the patient. In the fan beam convergent arrangement of applicators, electric field would be concave, focusing the energy to the particular area of the patient for treatment. The alignment of the magnetic and electric fields in the present invention enables the system to be more flexible from a design standpoint, because the thickness of the applicators can be changed without affecting the system.

Although the preferred embodiments of the invention have been illustrated in the accompanying drawings and described in the foregoing Detailed Description, it will be understood that the invention is not limited to the embodiments disclosed, but is capable of numerous rearrangements, modifications and substitutions of parts and elements without departing from the spirit of the invention.

I claim:

1. A multiple microwave applicator unit for use in a microwave hyperthermia treatment system including a source of microwave power, comprising:
a plurality of microwave waveguide applicators combined to form a microwave applicator unit;
means for microwave input power coupling said applicators to a source of microwave power;
means for selectively adding and removing individual applicators from among said plurality of applicators from coupling with said source of microwave power so as to incrementally increase or decrease the resultant treatment field size; and
means for positioning the geometry of said applicators, whereby the heating pattern may be controlled in a treatment area by shaping the propagated electromagnetic field and said plurality of applicators may be configured to conform to the contour of the treatment surface area, said plurality of microwave applicators being operated in a transverse electric mode whereby the electric field generated by the applicators is generally parallel the contour of the surface treatment area to minimize heating of healthy surface tissue.

2. The multiple microwave applicator unit of claim 1, wherein said microwave input power coupling is a magnetic coupling means.

3. The multiple microwave applicator unit of claim 1, wherein said plurality of applicators are operated in the incoherent mode, whereby the heating pattern is the sum of the heating pattern produced by each of said applicators.

4. The multiple microwave applicator unit of claim 1, wherein said applicators are operated in the coherent mode.

5. The multiple microwave applicator unit of claim 1, wherein said individual applicators are adjusted in a fan beam geometric configuration, whereby the microwave radiation is focused into an area of the patient selected for treatment.

6. The multiple microwave applicator unit of claim 5, wherein the angle of separation between said individual applicators is equal.

7. The multiple microwave applicator unit of claim 5, wherein the angle of separation between said individual applicators is unequal.

8. The microwave applicator unit of claim 1, wherein said applicators are operated in the fundamental transverse electric mode.

9. The microwave applicator unit of claim 1, wherein said applicators are operated in a higher order transverse electric mode.

10. The microwave applicator unit of claim 1, wherein said waveguide applicators are rectangular waveguides.

11. The microwave applicator unit of claim 1, wherein said waveguide applicators are cylindrical waveguides.

12. The microwave applicator unit of claim 1, wherein said waveguide applicators are elliptical waveguides.

13. The microwave applicator unit of claim 1, wherein said waveguide applicators are aligned to have their sidewalls substantially parallel, whereby a continuing electromagnetic field pattern is formed.

14. The microwave applicator unit of claim 1, wherein said plurality of applicators are sufficient in number and are adjusted to surround a region of a patient's body, whereby the electric field is substantially parallel to the contour of the region of the patient's body to be treated.

15. The microwave applicator unit of claim 14, whereby the open ends of said plurality of applicators are contiguous.

16. The method of operating a multiple microwave applicator unit of a microwave hyperthermia system in the incoherent mode to treat a patient, each applicator having an axis of propagation, comprising:
generating microwave power to each of said applicators from an independent microwave power source;
magnetically coupling microwave power from each of said independent power sources to each of said applicators such that the magnetic field propagated through each of said applicators is parallel to the axis of propagation;
operating each of said microwave applicators in the fundamental transverse electric mode; and
positioning the geometric configuration of said applicators relative to the contour of the patient surface treatment area for shaping the resultant magnetic field produced by said applicators, whereby the overall heating pattern for the hyperthermia system may be optimized for a particular treatment and the electric field will generally be parallel to the contour of the patient surface treatment area to minimize heat generation in healthy tissue.

17. The method of operating a hyperthermia treatment system with multiple microwave applicators in the incoherent mode, said applicators having an axis of propagation, comprising:
generating a single source of microwave power for distribution to each of the individual microwave applicators;
switching the source of microwave power sequentially from one of said applicators to another of said applicators;
magnetically coupling the microwave power source switched to each of said applicators, such that the magnetic field propagated through said applicators is parallel to the axis of propagation;
operating each of said microwave applicators in the fundamental transverse electric mode; and
positioning the geometric configuration of said applicators to shape the resultant electromagnetic field produced by the summation of each independent applicator for optimizing the heating pattern for a hyperthermia treatment.

18. The method of operating a hyperthermia treatment system with multiple microwave applicators in the incoherent mode, each applicator having an axis of propagation, comprising:

generating an electromagnetic microwave signal;

dividing said generated microwave signal equally for each of said applicators of the multiple applicator unit;

transmitting one of said divided microwave signals to an applicator selected as the reference applicator;

phase shifting each of said other divided microwave signals for modulating the phase of said microwave signals at a time to operate the applicators in the incoherent mode;

transmitting each of said phase shifted microwave signals to said other applicators;

operating each of said applicators in the fundamental transverse electric mode;

means for magnetically coupling each of said applicators to its phase shifted microwave signal source for aligning the magnetic field propagated through said applicators parallel to the applicator axis of propagation; and positioning the geometry of said applicators to shape the resultant propagated electromagnetic field to optimize the overall heating pattern for a hyperthermia treatment.

19. The method of operating a hyperthermia treatment system with multiple applicators in the coherent mode, said applicators having an axis of propagation, comprising:

generating a single microwave signal;

dividing said generated microwave signal equally among said applicators;

transmitting said divided microwave signal to one of said applicators selected as the reference applicator;

adjusting variable phase shifters with respect to the reference phase of the microwave signal transmitted to said reference applicator to provide a coherent electromagnetic wave propagated from said applicators;

means for magnetically coupling each of said applicators to its microwave signal, such that the magnetic wave propagated through said applicator is parallel to the axis of propagation;

operating the applicators in the fundamental transverse electric mode; and positioning the geometry of said applicators to shape the resultant propagated electromagnetic wave to achieve the optimum heating pattern for a hyperthermia treatment.

20. A microwave applicator system for use in conjunction with a source of microwave power for a microwave hyperthermia system, comprising:

a plurality of microwave waveguide applicators;

means for microwave input power coupling said applicators to a source of microwave power;

means for operating said applicators in a transverse electric mode; and means for positioning said applicators about a surface treatment area with the electric field component of the propagated wave substantially parallel to the contour of the surface treatment area, whereby the heating of healthy surface tissue from the electric field component is minimized.

21. The microwave applicator of claim 20, wherein the open ends of said applicators are contiguous, whereby the resultant field produced by said applicators is substantially continuous.

22. A method of operating a microwave applicator system for use in conjunction with a source of microwave power for a microwave hyperthermia system including the steps of:

coupling a plurality of microwave waveguide applicators to the source of microwave power;

operating said plurality of microwave waveguide applicators in a transverse electric mode; and positioning said plurality of applicators about a surface treatment area with the electric field component of the propagated wave substantially parallel to the contour of the surface treatment area, whereby the heating of healthy surface tissue from the electric field component is minimized.

23. The method of claim 22 further comprising the step of positioning the open ends of said plurality of microwave waveguide applicators continuous, whereby the resultant field produced by said applicators is substantially continuous.

* * * * *

UNITED STATES PATENT AND TRADEMARK OFFICE
CERTIFICATE OF CORRECTION

PATENT NO. : 4,397,313
DATED : August 9, 1983
INVENTOR(S) : Victor A. Vaguine

It is certified that error appears in the above—identified patent and that said Letters Patent is hereby corrected as shown below:

Column 2, line 23, change "electromagnet" to --electromagnetic--.

Signed and Sealed this

Twentieth Day of December 1983

[SEAL]

Attest:

GERALD J. MOSSINGHOFF

Attesting Officer

Commissioner of Patents and Trademarks